United States Patent
Lim et al.

(10) Patent No.: US 10,251,556 B2
(45) Date of Patent: Apr. 9, 2019

(54) IN VIVO BIOIMAGING METHOD AND SYSTEM USING NEAR-INFRARED LIGHT AND COMPLEMENTARY METAL-OXIDE-SEMICONDUCTOR IMAGE SENSOR

(71) Applicants: KOREA INSTITUTE OF SCIENCE AND TECHNOLOGY, Seoul (KR); CENTER OF HUMAN-CENTERED INTERACTION FOR COEXISTENCE, Seoul (KR)

(72) Inventors: Hwa Sup Lim, Seoul (KR); Seok Joon Kwon, Seoul (KR); Sang Chul Ahn, Seoul (KR); Bum Jae You, Seoul (KR)

(73) Assignees: Korea Institute of Science an Technology, Seoul (KR); Center of Human-Centered Interaction for Coexistence, Seoul (KR)

( * ) Notice: Subject to any disclaimer, the term of this patent is extended or adjusted under 35 U.S.C. 154(b) by 0 days.

(21) Appl. No.: 15/664,188

(22) Filed: Jul. 31, 2017

(65) Prior Publication Data
US 2018/0055367 A1    Mar. 1, 2018

(30) Foreign Application Priority Data

Sep. 1, 2016 (KR) ........................ 10-2016-0112806

(51) Int. Cl.
| | | |
|---|---|---|
| *H04N 7/18* | (2006.01) | |
| *A61B 5/00* | (2006.01) | |
| *H04N 5/33* | (2006.01) | |
| *H04N 5/225* | (2006.01) | |
| *H04N 5/374* | (2011.01) | |
| *H01L 27/146* | (2006.01) | |
| *H01L 31/0232* | (2014.01) | |

(52) U.S. Cl.
CPC ...... *A61B 5/0075* (2013.01); *H01L 27/14625* (2013.01); *H01L 31/02322* (2013.01); *H04N 5/2256* (2013.01); *H04N 5/332* (2013.01); *H04N 5/374* (2013.01); *A61B 5/4504* (2013.01); *H01L 27/14609* (2013.01); *H01L 27/14621* (2013.01); *H01L 27/14627* (2013.01); *H01L 27/14649* (2013.01)

(58) Field of Classification Search
CPC .................................................. A61B 5/0075
USPC ........................................................ 348/77
See application file for complete search history.

(56) References Cited

U.S. PATENT DOCUMENTS

| | | | | |
|---|---|---|---|---|
| 5,703,364 A | * | 12/1997 | Rosenthal ............ | G01N 21/359 250/339.12 |
| 2014/0161369 A1 | * | 6/2014 | Ishihara ................. | A61B 1/043 382/274 |
| 2014/0217264 A1 | * | 8/2014 | Shepard ............. | G01N 21/6458 250/208.1 |
| 2015/0238638 A1 | * | 8/2015 | Han ..................... | A61K 41/008 424/9.6 |
| 2016/0340569 A1 | * | 11/2016 | Belcher ................. | C09K 8/584 |

* cited by examiner

*Primary Examiner* — Leron Beck
(74) *Attorney, Agent, or Firm* — Rabin & Berdo, P.C.

(57) ABSTRACT

Provided is an in vivo bioimaging method including irradiating near-infrared (NIR) light onto a living body, converting the NIR light passed through the living body, into visible light using upconversion nanoparticles (UCNPs), and generating a bioimage of the living body by receiving the visible light using a complementary metal-oxide-semiconductor (CMOS) image sensor.

10 Claims, 5 Drawing Sheets

IN VIVO BIOIMAGING METHOD AND SYSTEM USING NEAR-INFRARED LIGHT AND COMPLEMENTARY METAL-OXIDE-SEMICONDUCTOR IMAGE SENSOR

CROSS-REFERENCE TO RELATED APPLICATIONS

This application claims priority to and the benefit of Korean Patent Application No. 10-2016-0112806 filed in the Korean Intellectual Property Office on Sep. 1, 2016, the entire contents of which are incorporated herein by reference.

BACKGROUND

1. Field

The present invention relates to an in vivo bioimaging method and system and, more particularly, to an in vivo bioimaging method and system using near-infrared (NIR) light and a complementary metal-oxide-semiconductor (CMOS) image sensor.

2. Description of the Related Art

Various types of imaging equipment are used to obtain bioimaged information in biology and medical fields. A bioimaging method using light provides information to a user or a surgeon in real time compared to other imaging techniques, and thus is broadly used. In addition, equipments or reagents used for optical imaging are low-priced and biocompatible compared to those used for other imaging techniques such as radiography. However, when visible light is used, the visible light may not be sufficiently transmitted through a living body and thus a phenomenon occurring in the living body may not be easily detected using fluorescent light. Near-infrared (NIR) light is best transmitted through a living body, and thus is used in a variety of bioimaging fields.

However, high-priced equipment should be used to obtain bioimages using NIR light.

SUMMARY

The present invention provides a method and system for obtaining in vivo bioimages at low costs using near-infrared (NIR) light. However, the scope of the present invention is not limited thereto.

According to an aspect of the present invention, there is provided an in vivo bioimaging method including irradiating near-infrared (NIR) light onto a living body, converting the NIR light passed through the living body, into visible light using upconversion nanoparticles (UCNPs), and generating a bioimage of the living body by receiving the visible light using a complementary metal-oxide-semiconductor (CMOS) image sensor.

The irradiating of the NIR light may include irradiating NIR light of various wavelength bands required to view anatomical features of the living body, and the converting of the NIR light may include passing only a specific wavelength band of the NIR light passed through the living body, using an NIR pass filter, and converting the NIR light of the specific wavelength band into visible light using the UCNPs.

The NIR light may have a wavelength band ranging from 900 to 1600 nm, and the visible light may have a wavelength band ranging from 500 to 700 nm.

The CMOS image sensor may include a silicon (Si)-based CMOS image sensor.

According to another aspect of the present invention, there is provided an in vivo bioimaging system including a complementary metal-oxide-semiconductor (CMOS) image sensor, upconversion nanoparticles (UCNPs) provided on the CMOS image sensor to convert near-infrared (NIR) light into visible light, an NIR pass filter provided on the UCNPs, and an NIR irradiator provided on the NIR pass filter.

The CMOS image sensor may include a silicon (Si)-based CMOS image sensor.

UCNPs may include a plurality of UCNPs provided in a form of a module, and the module of the UCNPs may be provided on each pixel of the CMOS image sensor.

The NIR irradiator may be capable of irradiating NIR light of various wavelength bands required to view anatomical features of a living body, and the NIR pass filter may be capable of passing only a specific wavelength band of the NIR light.

BRIEF DESCRIPTION OF THE DRAWINGS

The above and other features and advantages of the present invention will become more apparent by describing in detail embodiments thereof with reference to the attached drawings in which.

DETAILED DESCRIPTION

Figure 1:
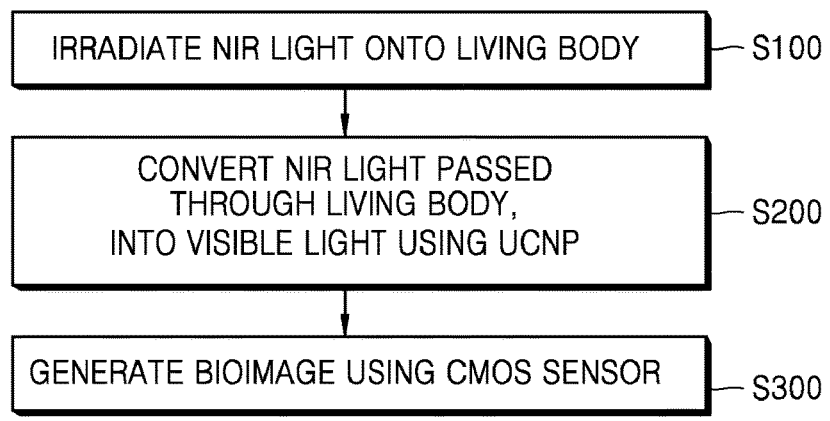
FIG. 1 is a flowchart of an in vivo bioimaging method according to an embodiment of the present invention.

The present invention will now be described more fully with reference to the accompanying drawings, in which embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to one of ordinary skill in the art. In the drawings, the sizes of elements may be exaggerated or reduced for convenience of explanation.

Hereinafter, the present invention will be described in detail by explaining embodiments of the invention with reference to the attached drawings.

FIG. 1 is a flowchart of an in vivo bioimaging method according to an embodiment of the present invention.

Referring to FIG. 1, the in vivo bioimaging method according to an embodiment of the present invention includes irradiating near-infrared (NIR) light onto a living body (S100), converting the NIR light passed through the living body, into visible light using upconversion nanoparticles (UCNPs) (S200), and generating a bioimage by receiving the visible light using a complementary metal-oxide-semiconductor (CMOS) image sensor (S300).

Figure 2:
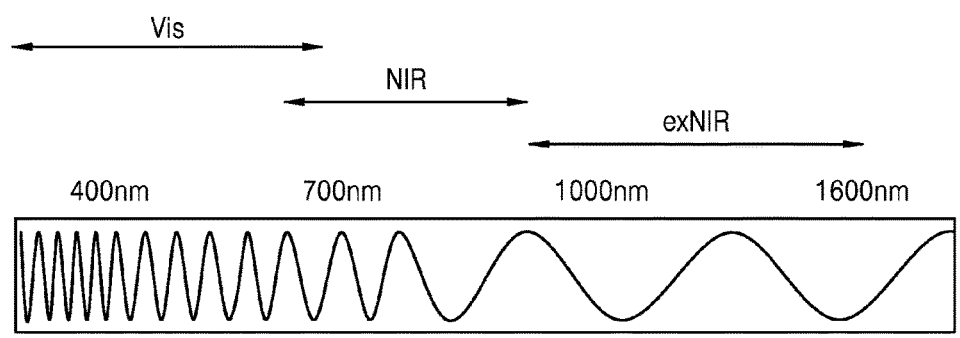
FIG. 2 is a view showing classification of light based on wavelength bands.
Figure 3:
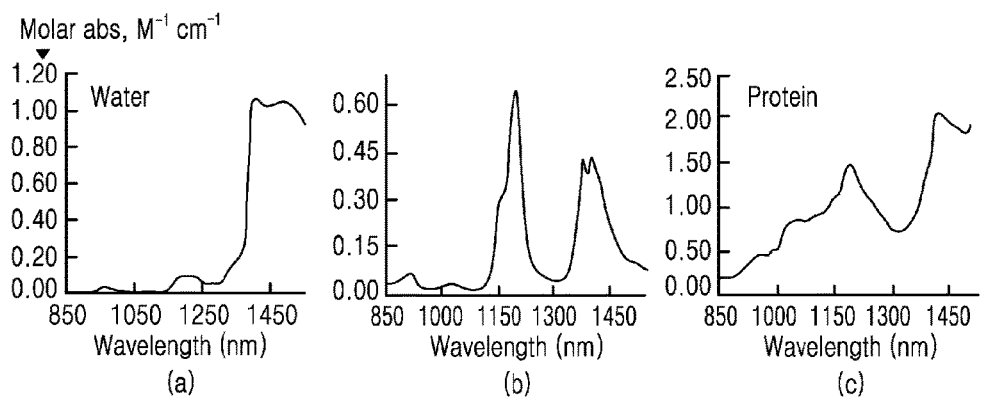
FIG. 3 includes views showing absorption rates of extended irradiating near-infrared (exNIR) light per wavelength by water, fat, and protein in tissues.

Referring to FIG. 2 showing classification of light based on wavelength bands, the NIR light used in the in vivo bioimaging method according to an embodiment of the present invention may be understood as extended NIR (exNIR) light having a wavelength band ranging from 900 to 1600 nm. The exNIR light is less spread in the living body than normal NIR light, and thus is more appropriate for bioimaging. Referring to FIG. 3 showing absorption rates of the exNIR light per wavelength by water, fat, and protein in a tissue, the absorption rate of the exNIR light per wavelength differs among water, fat, and protein in a tissue and thus may be used as an optical indicator capable of identifying the type of organ, gender, age of tissue, etc.

Tissues of the living body mostly consist of water, fat, and protein capable of absorbing the exNIR light, and thus may be imaged using the exNIR light. For example, since water has a high absorption rate in a wavelength band of 975 nm and transmission of a tissue is high in a wavelength band of 1075 nm, anatomical features may be viewed using a ratio of 1075 nm/975 nm and a result similar to an x-ray image may be obtained.

Using the above-described exNIR light, less harm may be caused to a human body than x-rays and an in vivo bioimage capable of viewing anatomical features may be rapidly and easily captured irrespective of locations.

To capture a bioimage by irradiating exNIR light, it may be required to use an indium-gallium-arsenide (InGaAs) image sensor having high photoelectric conversion efficiency in a wavelength band of 900 to 1600 nm. However, the InGaAs image sensor, which costs $40,000 per 1M pixels, is higher in price than a silicon (Si)-based CMOS image sensor, which costs $10 per 1M pixels. The Si-based CMOS sensor may refer to an image sensor produced by generating a CMOS device on a Si substrate.

The inventors propose an in vivo bioimaging method using UCNPs and a Si-based CMOS image sensor, which is lower in price than an InGaAs image sensor, and capable of achieving the same effect as using the InGaAs sensor.

That is, the in vivo bioimaging method according to an embodiment of the present invention includes irradiating NIR light onto a living body (S100), converting the NIR light passed through the living body, into visible light using UCNPs (S200), and generating a bioimage by receiving the visible light using a CMOS image sensor (S300).

Figure 4:
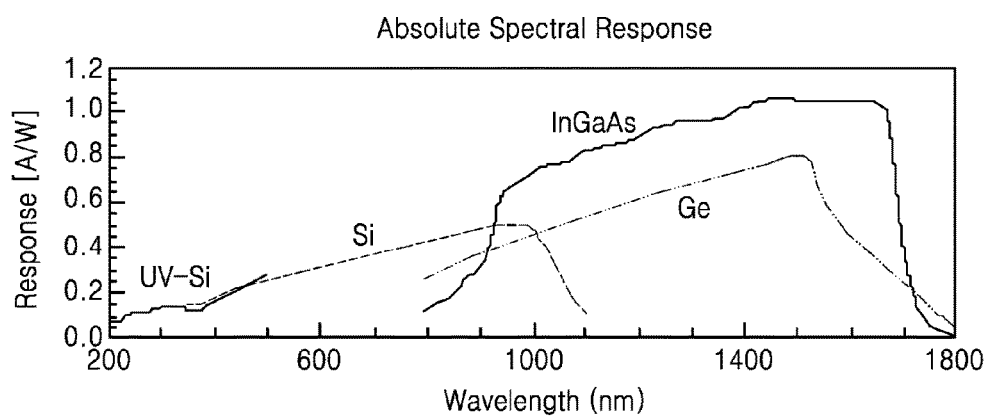
FIG. 4 is a view showing photoelectric conversion efficiency per wavelength based on material types.

Referring to FIG. 4 showing photoelectric conversion efficiency per wavelength based on material types, an InGaAs image sensor has excellent photoelectric conversion efficiency in a wavelength band of 900 to 1600 nm, and photoelectric conversion efficiency of a Si-based CMOS sensor is good in a wavelength band of 400 to 1000 nm and then is rapidly reduced. According to an embodiment of the present invention, it is found that, if light of a wavelength band of 1000 to 1400 nm is irradiated onto a living body and then is converted into light of a wavelength band of 500 to 700 nm using UCNPs, imaging is enabled using a Si-based CMOS sensor which is relatively low-priced.

Figure 5A:
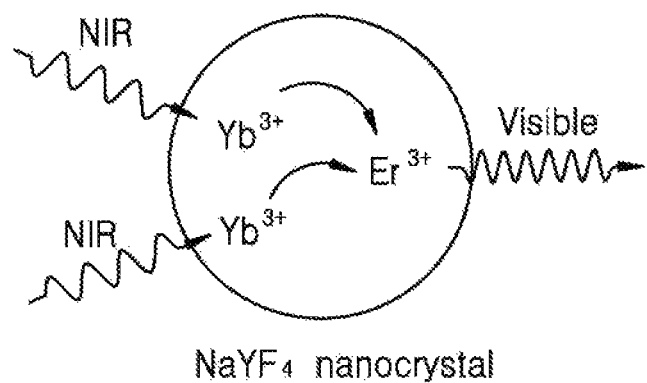
FIGS. 5A and 5B are views showing the principle of operation of upconversion nanoparticles (UCNPs)
Figure 5B:
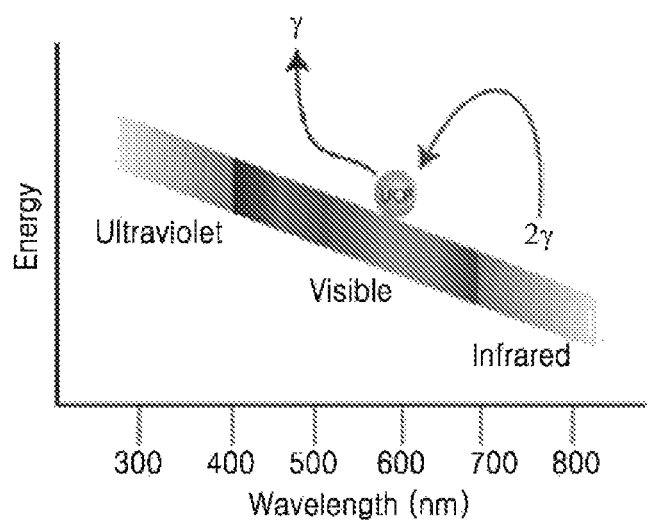

Referring to FIGS. 5A and 5B showing the principle of operation of UCNPs, a UCNP molecule absorbs two or more low-energy (infrared) photons and emits a high-energy (visible) photon. Accordingly, NIR light of a wavelength band of 1000 to 1400 nm may be converted into visible light of a 500 to 700 nm wavelength band using UCNPs. Since photoelectric conversion efficiency of a Si-based CMOS sensor is good in a wavelength band of 400 to 1000 nm and then is rapidly reduced, the Si-based CMOS sensor is not appropriate to image exNIR light. However, if the exNIR light is converted into a wavelength band of visible light using the UCNPs, the visible light may be imaged using a general CMOS image sensor.

Figure 6:
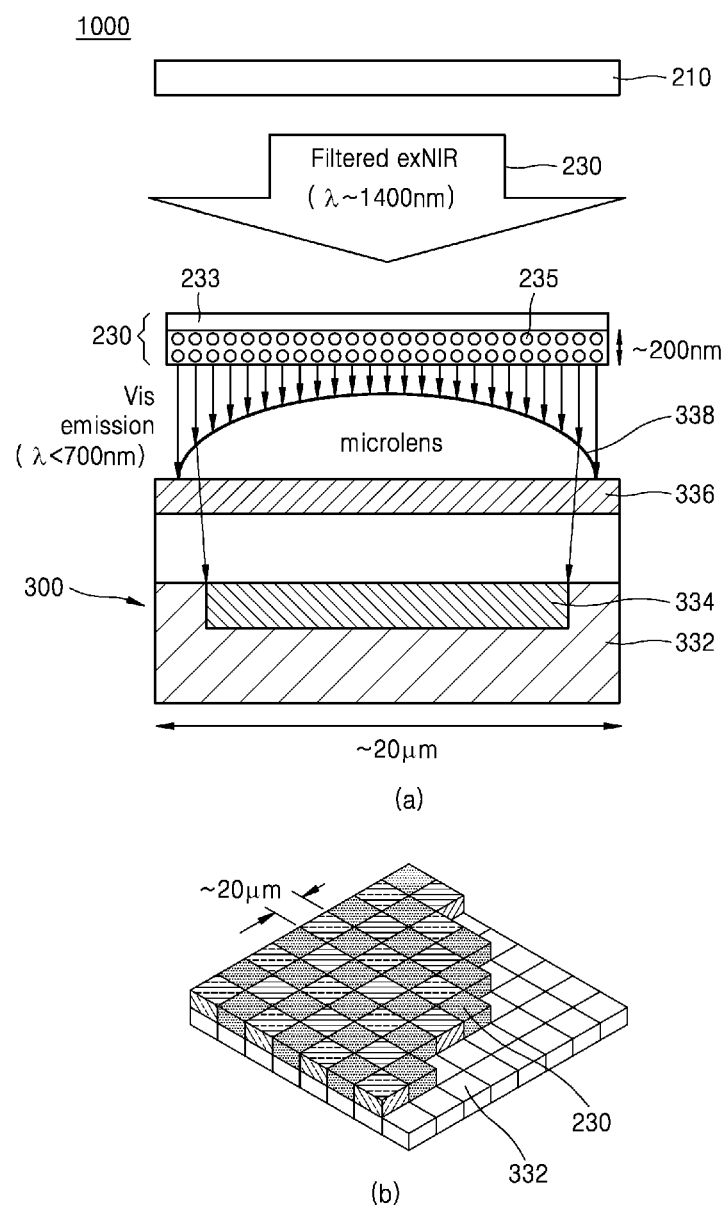
FIG. 6 includes views of an in vivo bioimaging system according to an embodiment of the present invention.
Figure 7:
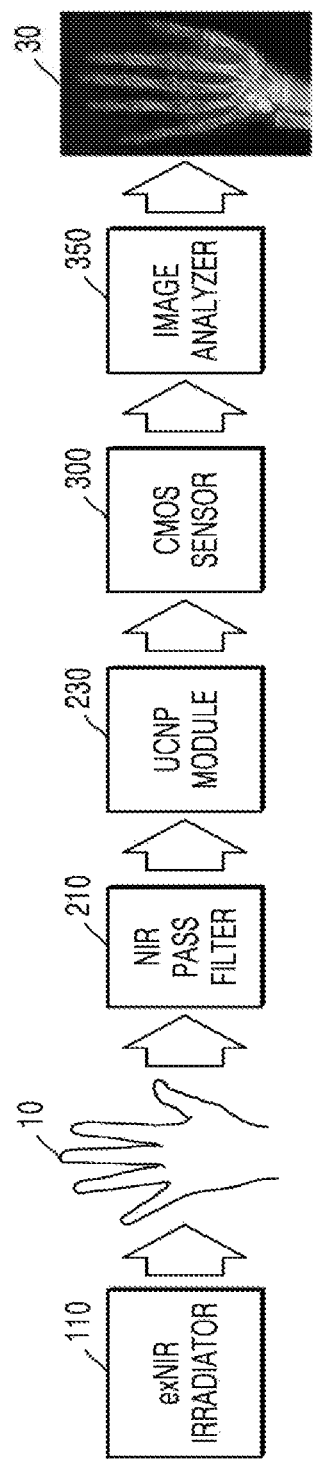
FIG. 7 is a block diagram for describing an in vivo bioimaging method using the in vivo bioimaging system, according to an embodiment of the present invention.

FIG. 6 includes views of an in vivo bioimaging system 1000 according to an embodiment of the present invention, and FIG. 7 is a block diagram for describing an in vivo bioimaging method using the in vivo bioimaging system 1000, according to an embodiment of the present invention.

Referring to FIGS. 6 and 7, the in vivo bioimaging system 1000 according to an embodiment of the present invention may include a CMOS image sensor 300, UCNPs 230 provided on the CMOS image sensor 300 to convert NIR light into visible light, and an NIR pass filter 210 provided on the UCNPs 230. An NIR irradiator may be further provided on the NIR pass filter 210.

The CMOS image sensor 300 may include a Si-based CMOS image sensor, and may include a photodiode 334 provided in each pixel 332. The CMOS image sensor 300 may further include a color filter 336 and a microlens 338 provided on the photodiode 334.

The UCNPs 230 may be provided in the form of a module. The module may include one or more layers of a plurality of UCNP arrays 235, and further include a plasmon emission enhancer 233. The module of the UCNPs 230 may be provided on each pixel 332 of the CMOS image sensor 300 (see (b) of FIG. 6).

Referring to FIG. 7, an exNIR irradiator 110 irradiates NIR light of various wavelength bands required to view anatomical features, onto a living body 10, the NIR pass filter 210 passes only desired wavelength bands of the NIR light, the UCNP module 230 converts the NIR light into visible light, and an image analyzer 350 generates an image 30 capable of viewing anatomical features, by combining exNIR light images of various wavelength bands.

A method and system for obtaining an in vivo bioimage similar to an x-ray image using NIR light and a Si-based CMOS image sensor have been described above. According to the above description, the in vivo bioimaging system is divided into an element for irradiating NIR light of a specific wavelength band, an element for passing the NIR light of the specific wavelength band, an element for converting the NIR light of the specific wavelength band into visible light, an element for obtaining a visible light image, and an element for generating a bioimage by combining visible light images. As such, a bioimage similar to an x-ray image may be obtained using a general CMOS image sensor in an indoor or outdoor environment. That is, since an exNIR light image is obtained using a general CMOS camera and analyzed to generate an image capable of viewing anatomical features similarly to an x-ray image, an in vivo bioimaging system may be simplified in structure and reduced in size, an image similar to an x-ray image but safer to human bodies compared to the x-ray image may be obtained, a bone fracture or the like may be easily diagnosed irrespective of locations and first aid treatment may be rapidly given.

According to the afore-described embodiments of the present invention, a bioimage similar to an x-ray image may be obtained using NIR light and a general CMOS image sensor in an indoor or outdoor environment. However, the scope of the present invention is not limited to the above effect.

While the present invention has been particularly shown and described with reference to embodiments thereof, it will be understood by one of ordinary skill in the art that various changes in form and details may be made therein without departing from the spirit and scope of the present invention as defined by the following claims.

What is claimed is:

1. An in vivo bioimaging method, the method comprising:
   irradiating, by a near-infrared (NIR) irradiator, NIR light onto a living body;
   converting the NIR light passed through the living body, into visible light using a module of upconversion nanoparticles (UCNPs), wherein the module of UCNPs is disposed at an opposite side of the living body from the NIR irradiator;
   receiving, by a complementary metal-oxide-semiconductor (CMOS) image sensor, the visible light converted by the module of UCNPs; and
   generating a bioimage of the living body by an image analyzer.

2. The method of claim 1, wherein the irradiating of the NIR light comprises irradiating NIR light of various wavelength bands required to view anatomical features of the living body, and
   wherein the converting of the NIR light comprises:
   passing only a specific wavelength band of the NIR light passed through the living body, using an NIR pass filter; and
   converting the NIR light of the specific wavelength band into visible light using the UCNPs.

3. The method of claim 1, wherein the NIR light has a wavelength band ranging from 900 to 1600 nm, and
   wherein the visible light has a wavelength band ranging from 500 to 700 nm.

4. The method of claim 1, wherein the CMOS image sensor comprises a silicon (Si)-based CMOS image sensor.

5. An in vivo bioimaging system comprising:
   a complementary metal-oxide-semiconductor (CMOS) image sensor;
   a module of upconversion nanoparticles (UCNPs) provided on the CMOS image sensor to convert near-infrared (NIR) light into visible light;
   an NIR pass filter provided on the module of UCNPs; and
   an NIR irradiator provided over the NIR pass filter and irradiating the NIR light onto a living body,
   wherein the module of UCNPs is disposed at an opposite side of the living body from the NIR irradiator, and
   the CMOS image sensor receives the visible light converted by the module of UCNPs.

6. The in vivo bioimaging system of claim 5,
   wherein the CMOS image sensor comprises a silicon (Si)-based CMOS image sensor.

7. The in vivo bioimaging system of claim 5,
   wherein the module of UCNPs comprises a plurality of UCNPs, and
   wherein the module of the UCNPs is provided on each pixel of the CMOS image sensor.

8. The in vivo bioimaging system of claim 5,
   wherein the NIR light has various wavelength bands required to view anatomical features of the living body, and
   wherein the NIR pass filter passes only a specific wavelength band of the NIR light.

9. The in vivo bioimaging system of claim 5, further comprising:
   a microlens provided on the CMOS image sensor.

10. The in vivo bioimaging system of claim 5, further comprising:
   an image analyzer generating an anatomical image of the living body.

* * * * *